US011554138B2

(12) United States Patent
Sun et al.

(10) Patent No.: US 11,554,138 B2
(45) Date of Patent: Jan. 17, 2023

(54) BISMUTH(III) COMPLEXES AS ADJUVANTS IN THE TREATMENT OF CANCER USING PLATINUM-BASED CHEMOTHERAPY

(71) Applicant: THE UNIVERSITY OF HONG KONG, Hong Kong (HK)

(72) Inventors: Hongzhe Sun, Hong Kong (HK); Chi-Fung Godfrey Chan, Hong Kong (HK); Shing Chan, Hong Kong (HK); Runming Wang, Hong Kong (HK)

(73) Assignee: THE UNIVERSITY OF HONG KONG, Hong Kong (HK)

( * ) Notice: Subject to any disclaimer, the term of this patent is extended or adjusted under 35 U.S.C. 154(b) by 0 days.

(21) Appl. No.: 15/210,019

(22) Filed: Jul. 14, 2016

(65) Prior Publication Data
US 2017/0014448 A1    Jan. 19, 2017

Related U.S. Application Data

(60) Provisional application No. 62/193,282, filed on Jul. 16, 2015.

(51) Int. Cl.
A61K 33/243        (2019.01)
A61K 33/24         (2019.01)
A61K 33/30         (2006.01)
A61K 33/245        (2019.01)
A61K 45/06         (2006.01)
A61P 35/00         (2006.01)

(52) U.S. Cl.
CPC ............ A61K 33/243 (2019.01); A61K 33/24 (2013.01); A61K 33/245 (2013.01); A61K 33/30 (2013.01); A61K 45/06 (2013.01); A61P 35/00 (2018.01)

(58) Field of Classification Search
CPC ...... A61K 33/24; A61K 33/245; A61K 33/30; A61K 33/243; A61K 45/06; A61P 35/00
See application file for complete search history.

(56) References Cited

U.S. PATENT DOCUMENTS 5,366,723 A * 11/1994 Tulok ................... A61K 31/198
                                                    424/649
6,426,076 B1    7/2002 Pascoe
2004/0258771 A1 12/2004 Fogarty
2014/0086940 A1  3/2014 Bryant
2014/0134265 A1  5/2014 Buggy et al.

OTHER PUBLICATIONS

Mowlood, Zanco J. Med. Sci., vol. 16, No. 1, 2012, pp. 31-39.*
Joshi et al. Biomedical and Environmental Sciences, 17, pp. 402-409, 2004.*
Asato et al. (Inorganic Chemistry, vol. 30 No. 22, 1991).*
Busse et al. Dalton Trans., 43, pp. 17980-17990 (Year: 2014).*
Keogan et al. 2014, Molecules, 19(9), pp. 15258-15297 (Year: 2014).*
Sadler et al. 1996, Chem. Eur. J. vol. 2 No. 6 pp. 701-708. (Year: 1996).*
Briand and Burford 1999, Chem. Rev., 99, pp. 2601-2657. (Year: 1999).*
Andrews et al. 2006, Dalton Trans., pp. 4852-4858. (Year: 2006).*
Gomes et al. J. Biol. Inorg. Chem. 2015, 20: 771-779. (Year: 2015).*
Bao Lin Zhang, et al. Determination of the Association Constant of Platinum(II) to Metallothionein, Journal of Inorganic Biochemistry, 1997, pp. 295-298.
Hongyan Li, et al. "Recent advances in bioinorganic chemistry of bismuth", Current Opinion in Chemical Biology, 2012, vol. 16, pp. 74-83.
Peter J. Boogaard, et al. "The role of metallothionein in the reduction of cisplatin-induced nephrotoxicity by Bi3+-pretreatement in the rat in vivo and in vitro", Biochemical Pharmacology, 1991, vol. 41, No. 3, pp. 369-375.
Akira Naganuma, et al. "Prevention of Lethal and Renal Toxicity of cis-Diamminedichloroplatinum(II) by Induction of Metallothionein Synthesis without Compromising Its Antitumor Activity in Mice", Cancer Research, 1987, vol. 47, pp. 983-987.
Bimanesh Sur, et al. "Effect of Liposomal Encapsulation of cis-Platinum Diamminodichloride in the Treatment of Ehrlich Ascites Carcinoma", Oncology, 1983, vol. 40, pp. 372-376.
Yukihiro Kondo, et al. "Citrate enhances the protective effect of orally administered bismuth subnitrate against the nephrotoxicity of cis-diamminedichloroplatinum", Cancer Chemother Pharmacol, 2004, vol. 53, pp. 33-38.
Masahiko Satoh, et al. "Protective role of metallothionein in renal toxicity of cisplatinum", Cancer Chemother Pharmacol, 1997, vol. 40, 358-362.
Yasuyuki Fujiwara, et al. "Protective role of metallothionein in chemical and radiation carcinogenesis" Current Pharmaceutical Biotechnology, 2013, 19 pages.
Felix Mitelman, et al. "The impact of translocations and gene fusions on cancer causation", Nature Reviews: Cancer, 2007, vol. 7, pp. 233-245.
Isolda Romero-Canelon, et al. "Systems approach to metal-based pharmacology", Proceedings of the National Academy of Sciences, 2015, vol. 112, No. 14, pp. 4187-4188.
P.A. Steerenberg, et al. "Liposomes as a drug carrier system for cis-diamminedichloroplatinum(II). I. Binding capacity, stability and tumor cell growth inhibition in vitro", International Journal of Pharmaceutics, 1987, vol. 40, pp. 51-62.
Hongzhe Sun, et al. "Interactions of Bismuth Complexes with Metallothionein(II)", The Journal of Biological Chemistry, 1999, vol. 274, No. 41, pp. 29094-29101.

* cited by examiner

Primary Examiner — Kara R McMillian
(74) Attorney, Agent, or Firm — Amin, Turocy & Watson, LLP

(57) ABSTRACT

The present disclosure relates to methods of using cisplatin active agents in which reduced organ toxicity is observed are provided. In the subject methods, an effective amount is administrated to the host before administration of an effective amount of cisplatin active agents. The cisplatin toxicity reducing agent comprising of stable bismuth(III) complexes or pharmaceutically acceptable salts reduces the levels of undesired toxicity of cisplatin active agents without compromising their anticancer activity. Also provided are methods for use in practicing the subject methods in the treatment of different disease conditions.

12 Claims, 11 Drawing Sheets

PBS

Cisplatin

BicitZ
+Cisplatin

PBS

Cisplatin

BicitZ
+Cisplatin

BISMUTH(III) COMPLEXES AS ADJUVANTS IN THE TREATMENT OF CANCER USING PLATINUM-BASED CHEMOTHERAPY

CROSS-REFERENCE TO RELATED APPLICATIONS

This application claims the benefit of priority to provisional application Ser. No. 62/193,282, filed on Jul. 16, 2015, which is incorporated herein by reference.

TECHNICAL FIELD

The subject matter herein relates in general to treatment of human diseases and pathological conditions. More specifically, described herein are bismuth(III) complexes as a cisplatin toxicity reducing agent to mitigate toxicity of cisplatin active agents, pharmaceutical compositions including the same, and the methods for using the same.

BACKGROUND

Platinum-based anticancer drugs are widely used in cancer chemotherapies. In particular, cisplatin (cis-[PtCl$_2$(NH$_3$)$_2$]) is one of the most effective drugs for testicular cancer with overall cure rate over 90% and it also plays a vital role in the treatment of several other forms of cancer including ovarian, head and neck, bladder, cervical, and non-small-cell lung cancer (Oncology, 1983, 40:372-376; Intl J Pharm, 1987, 40:51-62; Nat Rev Cancer, 2007, 7:573-584). Despite its effectiveness, it suffers significant side effects including nephrotoxicity, neurotoxicity, ototoxicity and electrolyte disturbance, among which nephrotoxicity is the severest one, sometimes even lethal and is the main dose-limiting factor.

Many attempts have been made to minimize the toxicity either by synthesis of new platinum based anticancer drugs or combined chemotherapy. Previous studies demonstrated that an inorganic bismuth salt was able to selectively reduce cisplatin-induced nephrotoxicity without compromising its antitumor activity in animal models, and such an effect is positively correlated to the renal expression level of metallothionein (Cancer Res 1987, 15:983-987). Furthermore, pretreatment of a bismuth salt would also allow high dosages of cisplatin to be administered without apparent toxicity in mice (Cancer Chemother Pharmacol 2004, 53:33-38; Cancer Chemother Pharmacol 1997, 40:358-362). Metallothionein is a cysteine-rich small protein with the function of protection of toxicity of heavy metals, oxidative stress as well as chemical and radiation carcinogenesis (Curr Pharm Biotechnol 2013 14:394-399). Platinum binds to metallothionein (MT) approximately 30 times more tightly than zinc and cadmium. The induction of MT in target organs by certain inducer may serve as an effective approach to mitigate renal toxicity of cisplatin owing to the ability of MT to sequestrate cisplatin as well as to protect against cisplatin-induced oxidative damage (Biochem Pharmaco 1991, 41:369375)

Bismuth is relatively nontoxic metal ion and has been associated with medicine for centuries (Curr Opin Chem Biol, 2012, 16: 74-83; Proc Natl Acad Sci USA, 2015, 112: 4187-4188). Bismuth-based complexes have been utilized clinically for the treatment of Helicobacter pylori infection for decades and are also preferentially accumulated in proximal tubular cells of kidney, which are found to be a good MT inducer (Anticancer Res 1992, 12:2303-2307). Thus, there is a high potential that bismuth complexes could readily be introduced in cancer chemotherapy as an antagonist against toxicity induced by platinum-based anticancer drugs, in particular cisplatin.

BRIEF SUMMARY

Despite that bismuth has been shown to be able to reduce renal toxicity of cisplatin without interference its efficacy, only bismuth inorganic salts were used for previous studies. Usually, bismuth inorganic salts exhibit poor solubility and might not be readily absorbed, thus it is obvious that an inorganic bismuth salt possesses a lower activity towards mitigation of cisplatin toxicity. Indeed, when co-administration of a chelating ligand such as citrate, bismuth activity is significantly improved (Cancer Chemother Pharmacol 2004, 53:33-38).

Described herein are methods of using bismuth(III) complexes in which reduced host organ toxicity is observed for a cisplatin active agent. In the subject methods, an effective amount of bismuth(III) complex is pre-administrated to the host before the administration of a cisplatin active agent. Also provided are pharmaceutical compositions, dosages and pretreatment time of the same compositions for use in practicing the subject methods, as well as application of the subject methods in different disease conditions.

DETAILED DESCRIPTION

Figure 1:
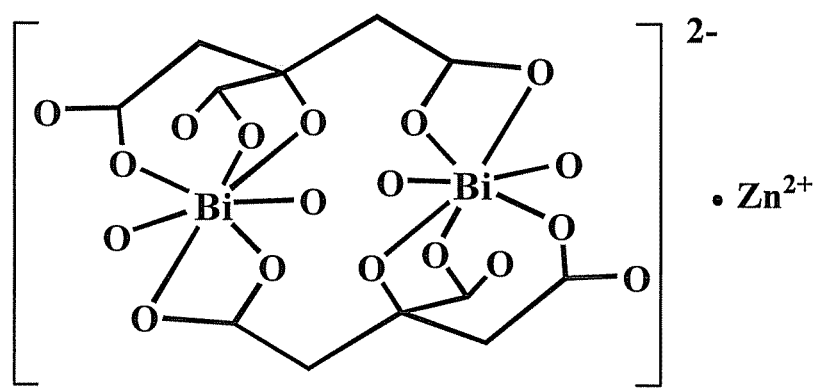
FIG. 1 Provides the chemical structure of the representative bismuth(III) complex, BicitZ FIG. 2 Depicts (a) the anti-apoptotic properties of BicitZ in HK-2 cells treated with cisplatin and control group of HK-2 cells. (b) HK-2 cells treated with cisplatin (20 μM). (c) pretreated with BicitZ and then treated with the same concentration of cisplatin as (b).
Figure 2:
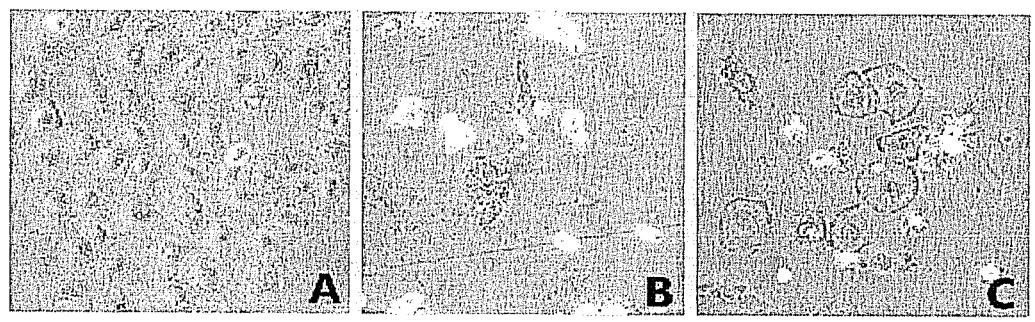

Described herein are methods of using bismuth(III) pharmaceutical agents in which reduced host organ toxicity is observed for a cisplatin active agent. In the subject methods, an effective amount of bismuth complexes is pre-administrated to the host several days prior to the administration of a cisplatin active agent. Also provided are pharmaceutical compositions, dosages and pretreatment time of the same compositions for use in practicing the subject methods as well as application of the subject methods in different disease conditions.

A host that suffers from disease or condition requiring the treatment of cisplatin typically has a form of cancer. As used herein, the term cancer refers to or describes the physiological condition in mammals in which a population of cells are characterized by unregulated cell growth. Examples of cancer include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancers.

The subject matter herein relates to administration of cisplatin toxicity reducing agents to a host that suffers from disease or condition requiring the treatment of cisplatin. The toxicity reducing agents of interest are stable bismuth(III) complexes or pharmaceutically acceptable salts. By bismuth (III) complexes is meant that complexes with bismuth(III) coordinated to but not limited to N, O, S containing ligands including but not limited to current clinically used bismuth antiulcer drugs for the treatment of *H. pylori* infection e.g. citrate based bismuth drugs (CBS e.g. De-Nol and RBC e.g. Pylorid) as well as bismuth subsalicylate (BBS). The ligands involved in the preparation of tested bismuth(III) complexes are shown below but not limited to them.

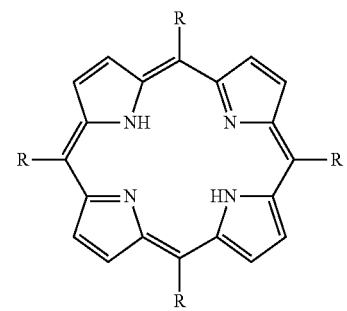

(L1)

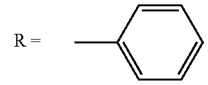

R =

(L2)

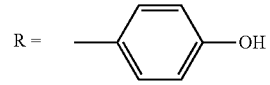

R = —⟨ ⟩—OH (L3)

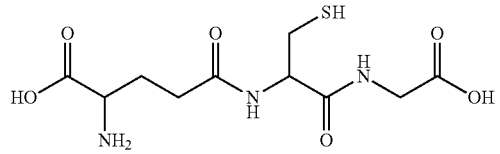

(L4)

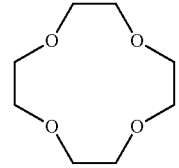

(L5)

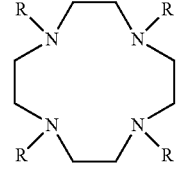

R = H (L6)

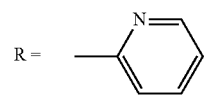

R =

(L7)

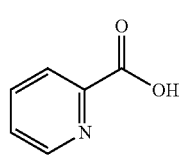

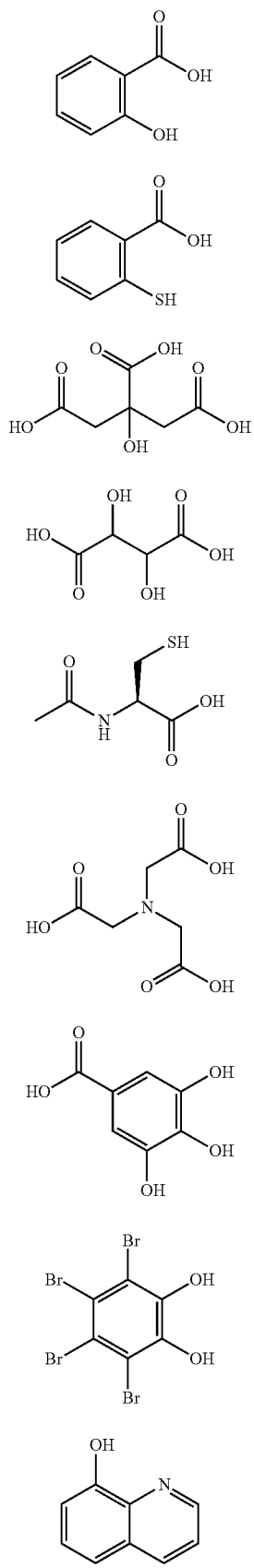

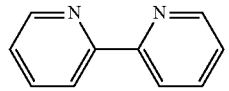

In one specific embodiment, the subject method to reduce cisplatin induced organ toxicity in kidney proximal tubular cells and tumor-bearing mice is pre-administration of a composition comprising an effective amount of a bismuth (III) zinc(II) citrate complex. The restriction of dietary zinc leads to reduced bismuth uptake and bismuth-induced metallothionein in rat kidney. Moreover, cancer patients often suffer zinc deficiency. The bismuth(III) zinc(II) citrate complex is described herein as BicitZ prepared by solubilization of bismuth citrate with zinc hydroxide and can be represented by the following dimeric structural formula:

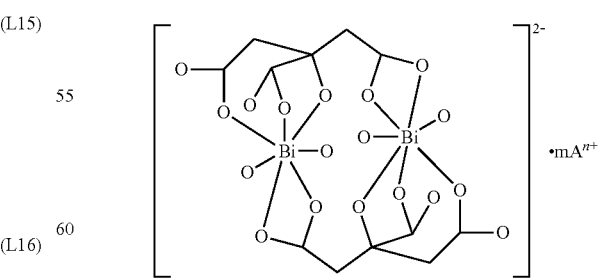

or a pharmaceutically acceptable salt thereof, wherein:
O without clear originality is from water or other citrate, in addition, $NH_3$ may be also included.

In the embodiment of citrate-based molecules and the bismuth(III) center usually exists as a dimer in solution. This does not exclude a possibility of formations of other molecular structures such as monomers or polymers at different pH values. Moreover, the bismuth(III) center at the embodiment of citrate-based molecules carries net negative charges, thus at least one counter-cation is required to neutralize the charge of the bismuth(III) centers. Accordingly, the phrase "pharmaceutically acceptable salt," as used herein, includes the salts formed from charged bismuth(III) complex and counter-cation Taken the dimer form of one embodiment as instance, as used herein, the term "citrate-based bismuth molecule" refers to a molecule of the following chemical structure:

wherein, "A" represents the "counter-cation", which refers to an ion associated with a negatively charged citrate-based bismuth(III) complex, is selected from a group consisting of $Zn^{2+}$ or $NH_4^+$, m*n=2.

As used herein, the term "citrate-based bismuth(III) zinc (II) complex (BicitZ)" refers to the complex of bismuth(III) bound to citrate molecule. The structure of the citrate based bismuth(III) complex can be a monomer, dimer or aggregated polymer.

As described herein, the term "bismuth pharmaceutical agents" is meant by bismuth(III) based complexes with pharmaceutically acceptable carrier, which refers to a carrier combination of carrier ingredients approved by a regulatory agency of the Federal or a state government or listed in the U.S. Pharmacopoeia or other generally recognized pharmacopoeia for use in animals, mammals, and more particularly in humans. Non-limiting examples of pharmaceutically acceptable carriers include liquids, such as water and oils, including those of petroleum, animal, vegetable, or synthetic origin. Water is a common vehicle when the compound is administered intravenously. Saline solutions and aqueous dextrose and glycerol solutions can also be employed as liquid vehicles, particularly for injectable solutions.

As summarized above, methods of administration of cisplatin toxicity reducing bismuth(III) complexes to a host that suffers from disease or condition requiring the treatment of cisplatin active agents are provided. An important feature of the subject methods is that bismuth complexes as cisplatin toxicity reducing agents need to be pre-administrated prior to administration of cisplatin active agents. By "pre-administrated" is meant that bismuth complexes as cisplatin toxicity reducing agents are administrated several days e.g. at least 1 day, at least 2 days or at least 3 days depending on the amounts administrated prior to administration of cisplatin active agents. Thus, the toxicity reducing bismuth(III) complexes are typically administered before cisplatin treatment begins.

In the subjected methods, reduction of cisplatin toxicity by bismuth(III) complexes is pre-administrated to a host that requires treatment of cisplatin active agents with an effective amount of a cisplatin toxicity reducing agents. By "cisplatin toxicity" is meant that toxicity induced by cisplatin or its derivatives/analogues such as carboplatin, ormaplatin, oxalipaltin, or other platinum-based anticancer drug as well as other metal containing anticancer drugs e.g. arsenic trioxide (Trisenox®).

The dosage cisplatin toxicity reducing agent is an amount effective to reduce organ toxicity of the cisplatin active agent, and/or eliminate organ toxicity of the cisplatin active agent. The dosage cisplatin toxicity reducing agent is typically greater than the dosage of the cisplatin active agent. In one embodiment, the dosage of cisplatin toxicity reducing agent is 2 or more fold of the cisplatin active agent. In another embodiment, the dosage of cisplatin toxicity reducing agent is 4 to 6 fold of the cisplatin active agent. In yet another embodiment, the dosage of cisplatin toxicity reducing agent is 4 to 14 fold of the cisplatin active agent.

Figure 7:
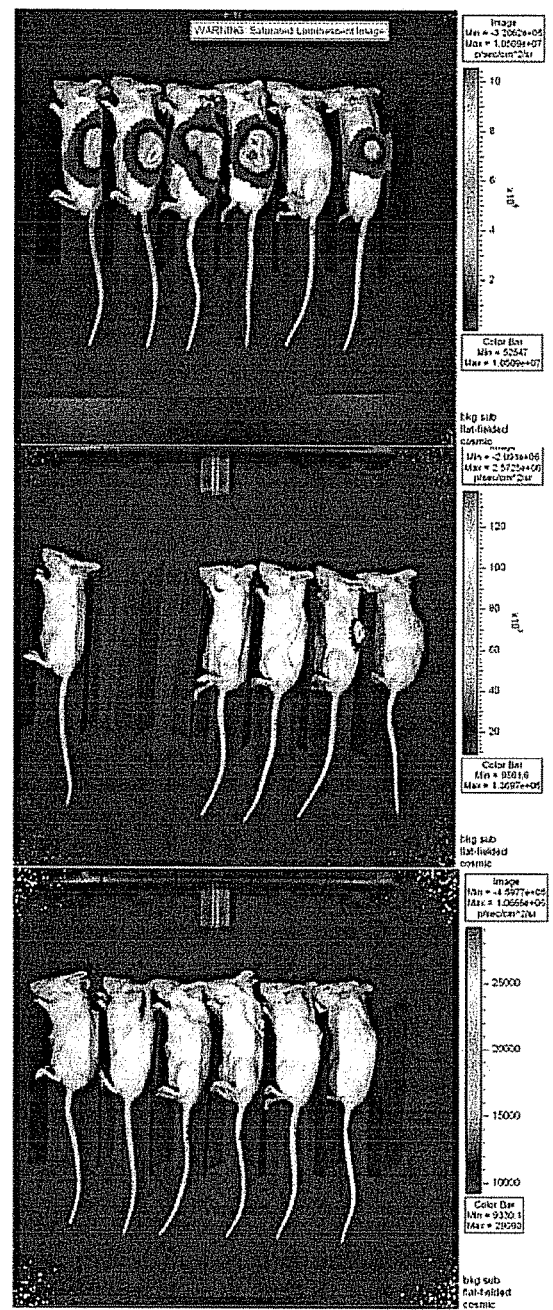
FIG. 7 Provides images showing that BicitZ has no interference on cisplatin's chemotherapeutic effect in tumor bearing mice. 0.2 Million SKNLP neuroblastoma cells transfected with luminescent plasmid were inoculated into the adrenal gland of SCID beige mice. BicitZ (100 mg/kg) was administered orally on Day −1, Day 0 and every two days since. Cisplatin (7.5 mg/kg) was i.p. injected at Day 0, Day 7 and Day 14. Tumor growth was monitored by luminescent of the transfected tumor cells.
Figure 8:
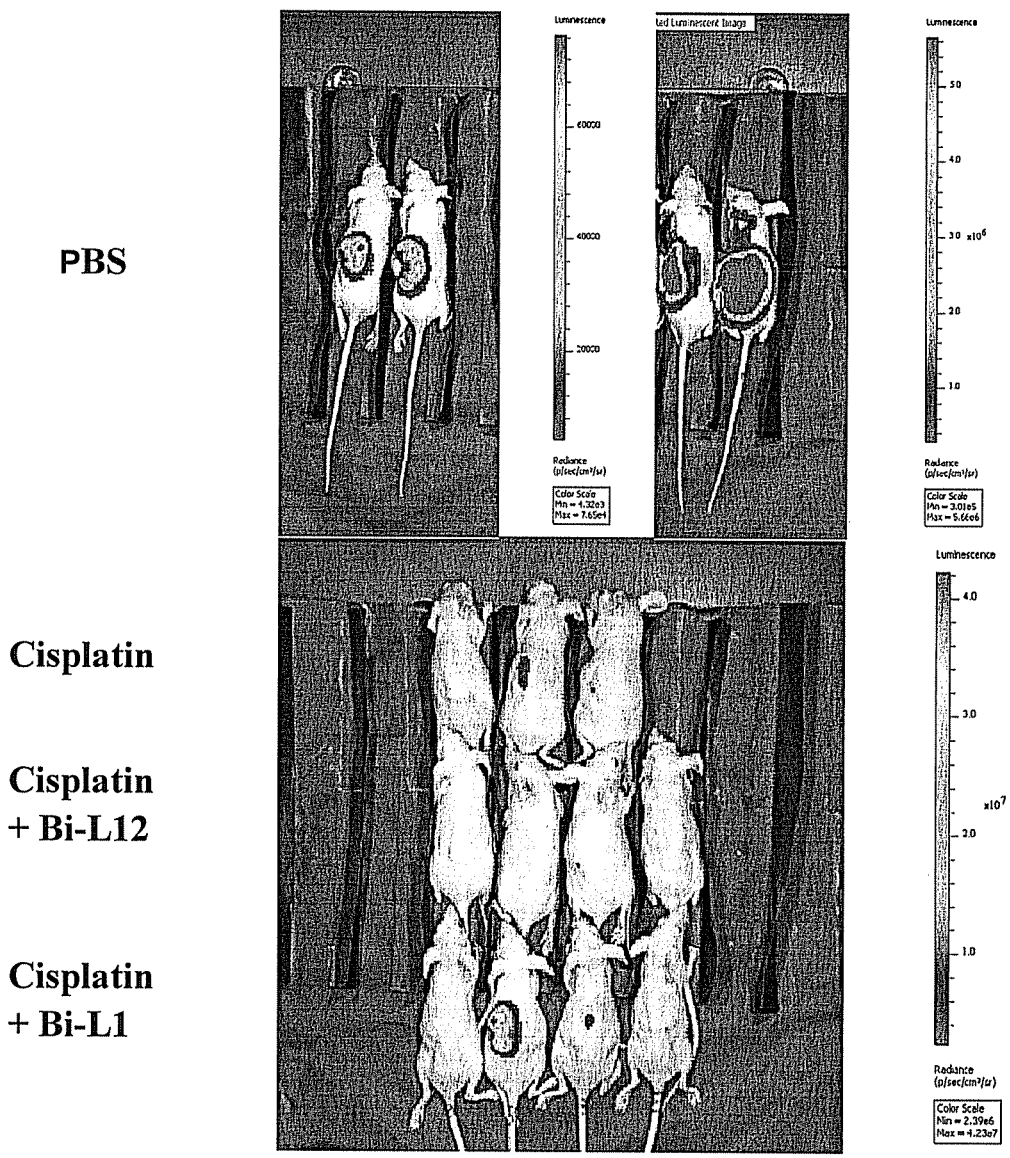
FIG. 8 Provides images showing that Bi-L1 and Bi-L12 have no interference on cisplatin's chemotherapeutic effect in tumor bearing mice. SKNLP neuroblastoma cells (~2×10$^5$ cells) were transfected with luminescent plasmid were inoculated into the adrenal gland of BALB/c nude mice. Bi-L1 and Bi-L12 (100 mg/kg) were administered orally at Day −1, Day 0 and every two days since. Cisplatin (7.5 mg/kg) was i.p. injected on Day 0, and Day 7. Tumor growth was monitored by luminescent of the transfected tumor cells.

According to the subject matter herein, cisplatin and any analogues/derivatives or other metal-containing anticancer drugs whose toxicity is reduced when bismuth(III) complexes are administered prior to administration of cisplatin active agents. Cisplatin toxicity reducing bismuth complexes are suitable to use in the subject methods as they exert no effects on the efficacy of cisplatin in mouse model described in the experimental section below. As described in FIG. 7 and FIG. 8, pretreatment of specific embodiments including BicitZ, Bi-L1 and Bi-L12, at 100 mg/kg exhibits no interference on cisplatin's chemotherapeutic effect (7.5 mg/Kg) in SCID beige tumor-bearing mice.

Figure 5:
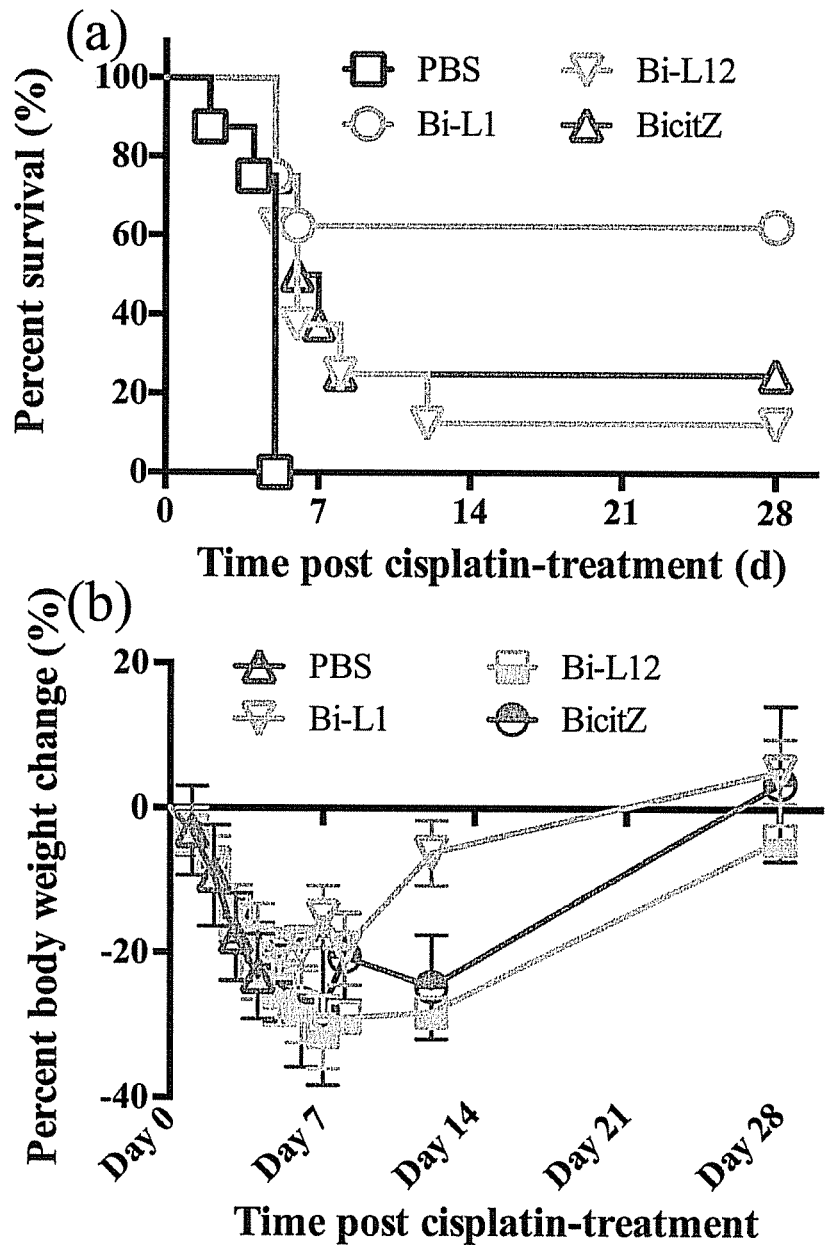
FIG. 5 Provides survival curves of cisplatin-treated mice with pretreatment of Bi-L1, Bi-L12 and BicitZ, respectively, showing the protective role of bimusth(III) complexes on cisplatin induced nephrotoxicity. All bismuth complexes (50 mg/kg) were administered orally on Day −2, Day −1, Day 0, Day 2 and Day 4. Cisplatin (30 mg/kg) was I.P. injected on Day 0. Kaplan-Meier survival curves show a higher survival rate of mice with pretreatment of bismuth(III) complexes, n=8. (Log-rank (Mantel-Cox) test, ***P=0.0004)

As indicated above, an effective amount of cisplatin toxicity reducing bismuth complexes are employed in the subject method. The amounts of cisplatin toxicity reducing bismuth(III) complexes may vary according to administrated dosages of cisplatin. The bismuth(III) complexes can be pre-administrated at a single high dosage or at lower multiple dosages before injection of cisplatin. In one embodiment, bismuth(II) complexes was administered orally prior to i.p. injection of cisplatin. Mice exhibit significant improvement in survival rate compared with those without pretreatment of the embodiment as shown in FIG. 5.

By cisplatin toxicity reducing bismuth(III) complexes is meant those bismuth complexes that reduce unwanted toxicity of cisplatin or its derivatives or other metal-containing anticancer drugs. Those bismuth complexes when pre-administrated to a host before administration of cisplatin active agents can reduce the toxicity of cisplatin active agents including but not limited to nephrotoxicity as described in one embodiment (FIG. 6), in which pretreatment of a bismuth complex reduced cisplatin-induced nephrotoxicity as manifested by the decreased levels of blood urea nitrogen (BUN).

According to the subject method, pre-administration of cisplatin toxicity reducing bismuth(III) complexes to a host that requires treatment of cisplatin active agents reduced host organ toxicity. The term "organ" refers to but not limited to kidney, liver, heart, nerves, bladder, reproductive organs, blood, stomach, intestines, bone marrow, or lung.

Regarding the underlying mechanism of bismuth complexes as a protector of cisplatin induced organ toxicity, it was found in previous studies that bismuth can selectively reduce cisplatin-induced nephrotoxicity without compromising its antitumor activity, and this effect is positively correlated to the renal expression level of a small protein-metallothionein (*Cancer Res* 1987, 15:983-987). Metallothionein (MT) is a family of cysteine-rich, low molecular weight proteins with the capability of binding to physiological $Zn^{2+}$ and $Cu^{2+}$, xenobiotical $Bi^{3+}$, $Pt^{2+}$, $Cd^{2+}$ etc. and is universally expressed, but relatively rich in liver and kidney. $Bi^{3+}$ has been shown to be able to displace $Zn^{2+}$ and $Cd^{2+}$ from the MT II even at extremely low pH, and binds to MT II with a stoichiometry of bismuth: MT=7:1 (*J Biol Chem* 1999, 274:29094-29101). The affinity of platinum to MT was demonstrated to be approximately 107 and 30 times more firm than zinc and cadmium respectively (*J Inorg Biochem* 1997, 65:295-298). However, reduced renal toxicity observed in animal model might not be attributable to increased binding of Pt(II) to renal MTs induced by bismuth, instead, the anti-oxidant activity of MT might be responsible for the reduction of cisplatin-induced renal toxicity (*Biochem Pharmacol* 1991, 41:369-375). Since renal superoxide dismutase (SOD) activity is increased in rats that received cisplatin, leading to peroxidative damage, but not in rats receiving $Bi^{3+}$ prior to cisplatin. Taken together it can be the anti-oxidative stress property of MTs that reduces the cisplatin-induced nephrotoxicity.

In our recent study, the intracellular amounts of bismuth under bismuth treatment are found to relate to glutathione (*Proc Natl Acad Sci*, 2015, 112: 3211-3216). The exact mechanism underlying bismuth capability of protecting cisplatin-induced organ toxicity is still not fully understood. It is not known whether thiolate-containing biomolecules other than MTs might also play roles in mitigation of cisplatin or its analogue induced organ toxicity.

EXAMPLES

The following examples illustrate the subject invention. Unless otherwise indicated in the following examples and elsewhere in the specification and claims, all parts and percentages are by weight, all temperatures are in degrees Centigrade, and pressure is at or near atmospheric pressure.

Example 1: Preparation of Bismuth(III) Complexes

In general, the preparation of bismuth(III) complexes are conducted by coordinating bismuth(III) ions to N, O and/or S-contained ligands via wet chemistry route. Herein, we take the synthesis of bismuth(III) zinc(II) citrate complex, BicitZ, as instance. Typically, zinc hydroxide solution was mixed with bismuth substrate, followed by adjusting pH to 7.2 using diluted ammonia and 18% HCl solution. The solubility of the complex is over 100 mM in water and is highly dependent on pH and ionic strength. Crystal structure of these complexes is not available yet, however, it is likely to assume similar structures as clinically used antiulcer drugs CBS or RBC (*J Am Chem Soc* 2003, 125:12408-12409). In these structures, bismuth(III) coordinates with tridentate citrate, forming a well-defined dinuclear unit $[Bi(cit)_2]^{2-}$ with additional $O^{2-}$, $OH^-$ and $H_2O$ ligands as shown in FIG. 1. Other cations such as $NH^{4+}$ serve as counter ions to balance negative charge bismuth(III) center. Zinc(II) may play a similar role to stabilize the structure.

Example 2: Bismuth(III) Complexes Exert Potent Protective Role Against Cisplatin Caused Cytotoxicity in Human Cell To evaluate the in vitro protection effect of test bismuth (III) complexes against cisplatin stress, two nontumorigenic normal human cell lines, HK-2 (human kidney proximal tubular cell) and MIHA (human hepatocyte cell) are incorporated herein for cell proliferation kit II XTT assay.

The XTT assay was carried out according to the manufacturer's instruction (Roche Diagnostics, USA). Typically, $1-2 \times 10^4$ cells per well were grown in flat-bottom 96-well plates at 37° C. for an overnight under a humidified atmosphere of 5% $CO_2$. Cells pellets were washed with PBS and treated with bismuth(III) complexes at various concentrations (1-100 μM) for 2 hours prior to the exposure to cisplatin (10 μM and 100 μM for HK-2 and MIHA cell line, respectively) for 2 days. Cells grown under culture medium alone were used as a negative control. After a fixed incubation time, 50 μl of the XTT labeling mixture was added to each well and the cells were incubated for 2 hours. The formation of formazan dyes, produced only by metabolic active cells, was detected spectrophotometrically at 490 nm.

Figure 3:
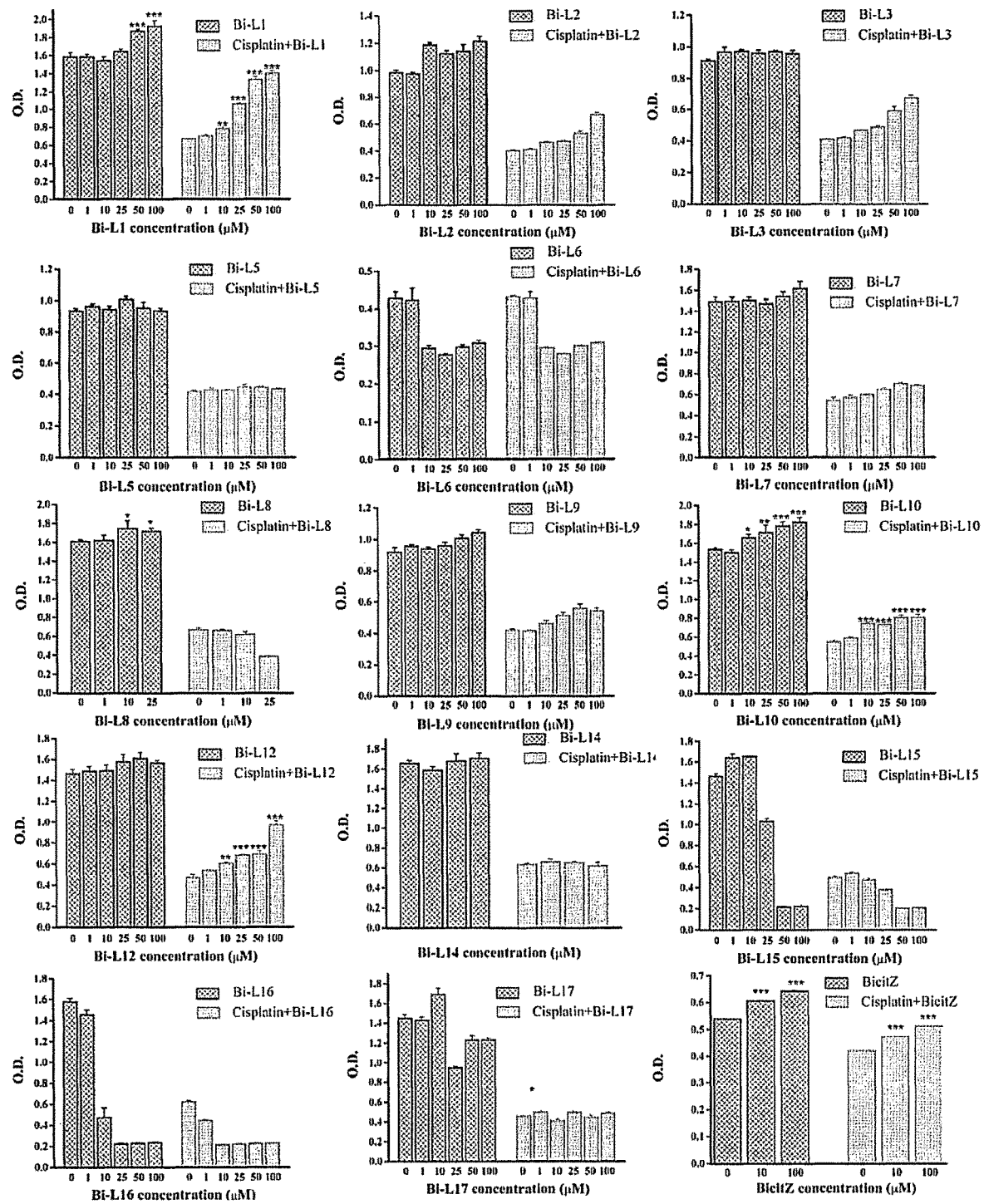
FIG. 3 Depicts the anti-apoptotic properties of bismuth (III) complexes in MIHA cells treated with bismuth(III) complexes with increasing concentrations (1-100 μM) in the absence and presence of cisplatin (100 μM). MIHA cells treated with culture medium served as a control. The respective survival rate was measured by cell proliferation kit XTT. All data are in triplicates.
Figure 4:
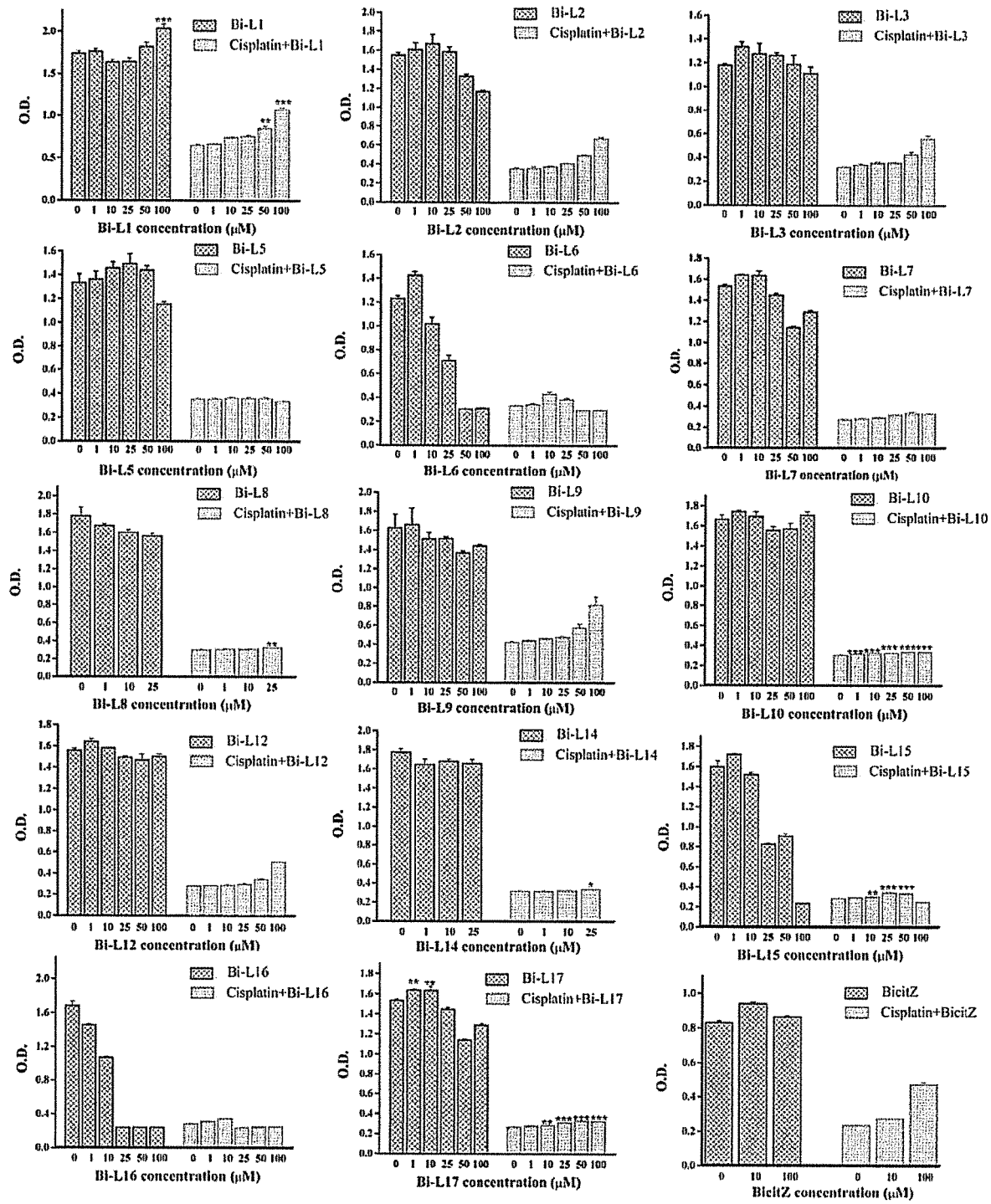
FIG. 4 Depicts the anti-apoptotic properties of bismuth (III) complexes in HK-2 cells treated with bismuth(III) complexes with increasing concentrations (1-100 μM) in the absence and presence of cisplatin (10 μM). HK-2 cells treated with culture medium served as a control. The respective survival rate was measured by cell proliferation kit XTT. All data are in triplicates.

As shown in FIG. 3 and FIG. 4, bismuth(III) complexes show no or slight cytotoxicity towards two cell lines except Bi-L15 and Bi-L16 when used alone. Less than 40% cells survived after exposure to cisplatin only. However, upon the co-treatment, tested bismuth(III) complexes were able to counteract the cisplatin induced cytoxicity at different degrees. In particular, the cell viabilities were increased distinctly by 46.3%, 34.0% and 16.7% for HK-2 and 29.0% 14.7% and 28.5% for MIHA, respectively, when Bi-L1, Bi-L-12 and BicitZ were co-treated with cisplatin.

Example 3: Pre-Administration of Bismuth(III) Complexes Shows the Protective Property on Cisplatin Induced Nephrotoxicity in Mice Given the potent in vitro effect of Bi-L1, Bi-L12 and BicitZ, their protective roles against cisplatin caused nephrotoxicity was further examined in an in vivo murine model.

In a typical experiment, 4 groups of 6 to 8-week-old female BALB/c mice (Laboratory Animal Unit, the University of Hong Kong) were housed and given free access to water and food. All animal experiments were done in accordance with the University of Hong Kong Guideline for Animal Care and Experimentation. Cisplatin (30 mg/kg) was injected i.p. on Day 0. 50 mg/kg of Bi-L1, Bi-L-12, BicitZ and PBS (serves as a control) were administered orally in a 200-μL aliquot on Day −2, −1, 0, 2 and 4. Survival rates of different groups of mice were monitored; Kaplan-Meier estimates of the survival curves were calculated and plotted. n=8 (FIG. 3). Significant increases in the survival rates of the mice are noted for the group with pre-treatment of bismuth(III) complexes prior to injection of cisplatin.

Figure 6:
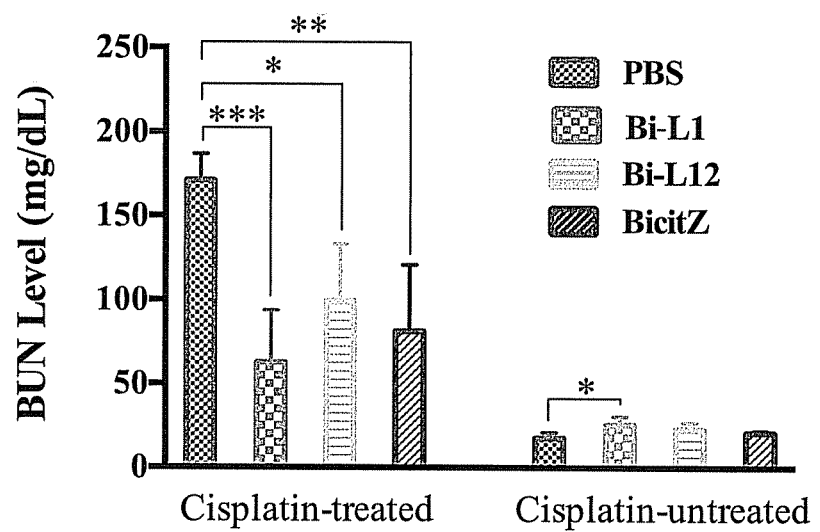
FIG. 6 Provides graphs showing the effect of pretreatment of bismuth(III) complexes on renal function of mice with administration of cisplatin, which was measured by the level of BUN (blood urea nitrogen). All the experimental conditions were kept the same as described in survival assay. All the mice were sacrificed on day 5 and serums were collected for BUN assay. The BUN level was measured using Urea Nitrogen Kit (Stanbio Laboratory, USA, Stanbio, Ref. 2020-430). Each BUN represents as the mean±SD. *P<0.05 P<0.01 and *P<0.001.

It is also noted that the levels of blood urea nitrogen (BUN) in cisplatin-treated mice is increased significantly compared with those of PBS and Bi(III) complexes pre-administered groups. The pre-administration of Bi(III) complexes significantly reduced the BUN levels, suggesting a renal protective role of Bi(III) complexes on cisplatin-treated mice as shown in FIG. 6.

Example 4: Pre-Administration of Bismuth(III) Complexes Exhibits no Interference on Cisplatin's Anti-Cancer Effectiveness To evaluate whether Bi(III) complexes affect cisplatin's in vivo anti-tumor activity, SKNLP neuroblastoma cells transfected with luminescent plasmid were implanted into mice. Groups of tumor-engrafted mice were administered orally with Bi-L1, Bi-L12, BicitZ (50 mg/Kg) and PBS (as control) on Day −1, Day 0 (2 hours prior to cisplatin treatment) and every two days post cisplatin (7.5 mg/kg) treatment on Day 0, respectively. SCID Berge mice were used in the BicitZ-treated group and received cisplatin treatment on Day 0, 7 and 14. BALB/c nude mice were used in Bi-L1- or Bi-L12-treated group and received cisplatin treatment on Day 0 and 7.

Figure 9:
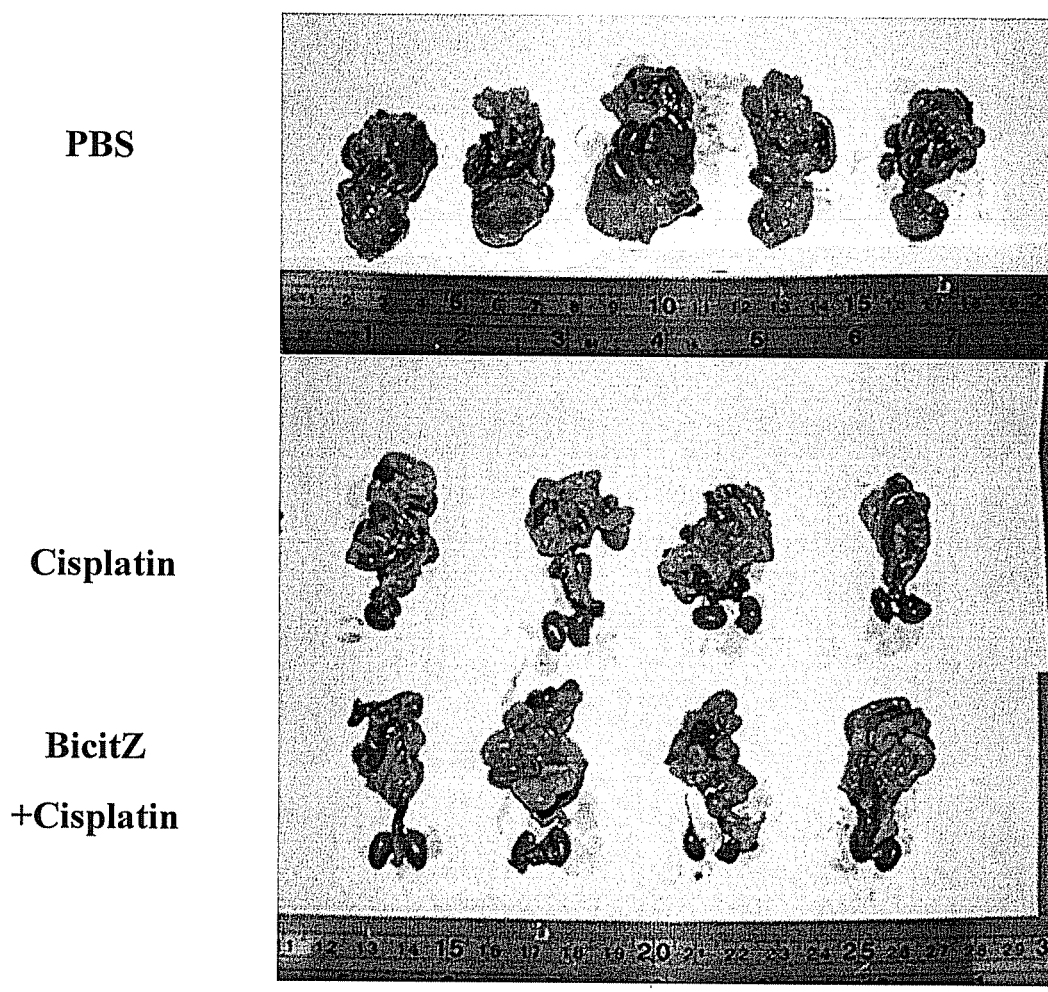
FIG. 9 Provides photos of the dissected tumors after tumor-bearing mice receiving treatment of PBS, cisplatin and cisplatin with BicitZ.
Figure 10:
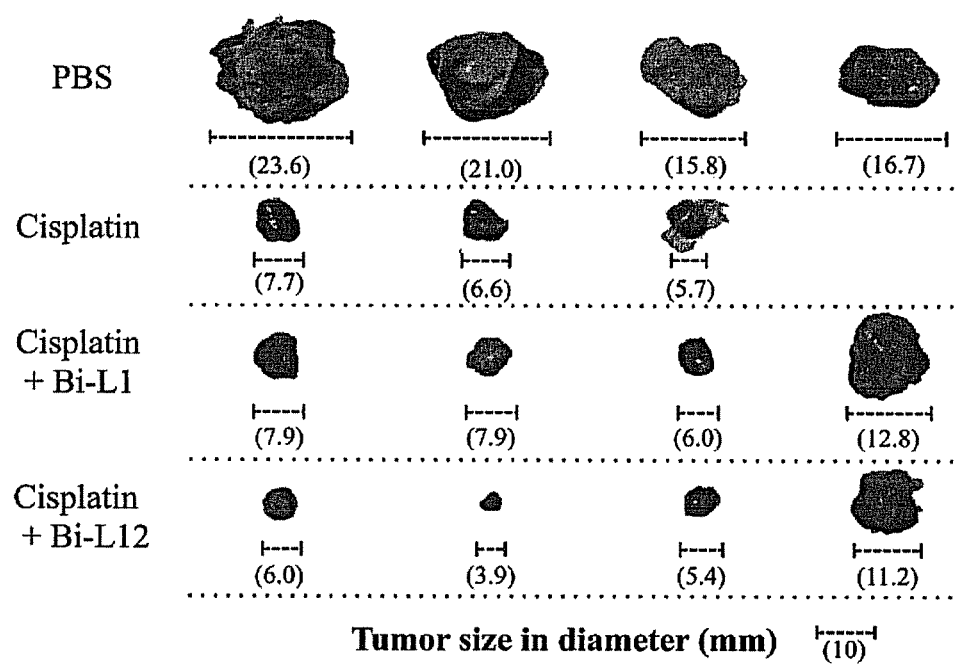
FIG. 10 Provides size of the dissected tumors after tumor-bearing mice receiving treatment of PBS, cisplatin and cisplatin with Bi-L1 and Bi-L12.
Figure 11:
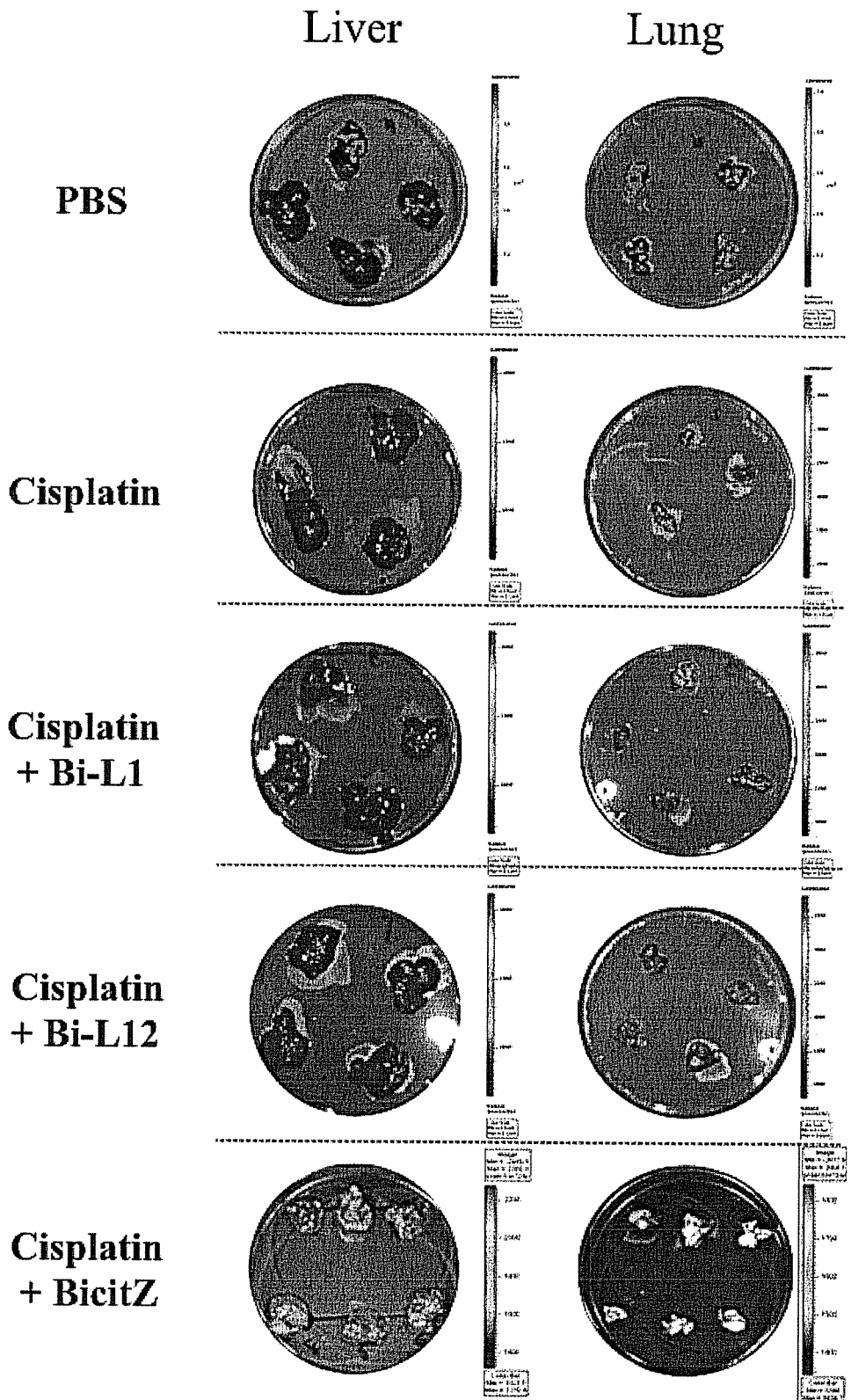
FIG. 11 Provides images showing that administration of Bi-L1, Bi-L12 and BicitZ delays SKNLP tumor cells metastases in lung and liver. The mouse livers and lungs were collected from the same experiment as in FIG. 7 and FIG. 8.

The results show that pre-administration of BicitZ (FIG. 7), Bi-L1 and Bi-L12 (FIG. 8) exerts negligible effects on cisplatin's anti-cancer activity in tumor engrafted mice. The sizes of the dissected tumor also confirmed this statement (FIG. 9 and FIG. 10). Further histology image of mouse liver and lung as present in FIG. 11 shows that pre-administration of Bi(III) complexes reduced or have no interference on tumor extensive metastasis in comparison with the control and cisplatin alone groups.

With respect to any figure or numerical range for a given characteristic, a figure or a parameter from one range may be combined with another figure or a parameter from a different range for the same characteristic to generate a numerical range.

Other than in the operating examples, or where otherwise indicated, all numbers, values and/or expressions referring to quantities of ingredients, reaction conditions, etc., used in the specification and claims are to be understood as modified in all instances by the term "about."

While the invention has been explained in relation to certain embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A method of administrating to a subject in need thereof an effective amount of a cisplatin active agent, comprising administering to a host an effective amount of a cisplatin toxicity reducing agent to reduce toxicity of the cisplatin active agent to a host organ, wherein the host organ is selected from a kidney, liver, heart, nerves, bladder, reproductive organs, blood, stomach, intestines, bone marrow, or lung, the cisplatin toxicity reducing agent comprises bismuth (Ill) complexes, or pharmaceutically acceptable salts thereof, with bismuth (Ill) coordinating to Ligand L2:

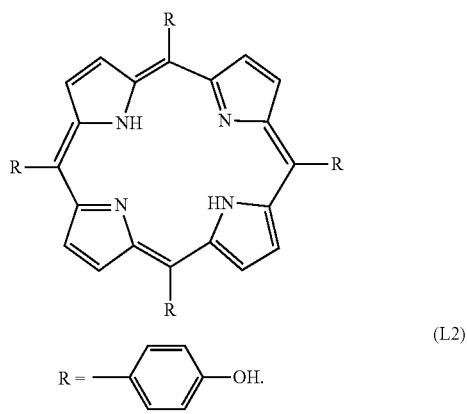

(L2)

agent together with a cisplatin toxicity reducing agent to reduce organ toxicity of the cisplatin active agent to a host organ, wherein the host organ is selected from a kidney, liver, heart, nerves, bladder, reproductive organs, blood, stomach, intestines, bone marrow, or lung, the cisplatin toxicity reducing agent comprises bismuth (Ill) complexes, or pharmaceutically acceptable salts thereof, with bismuth (Ill) coordinating to Ligand L2:

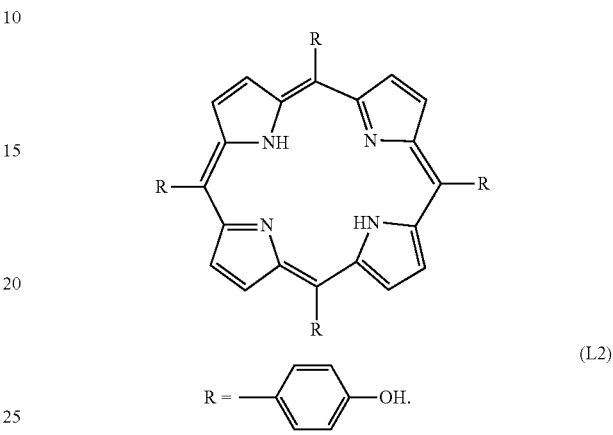

(L2)

2. The method according to claim 1, wherein the dosage of cisplatin toxicity reducing agent is 4 to 6 fold of the cisplatin active agent.

3. The method according to claim 2, wherein the cisplatin active agent and the cisplatin toxicity reducing agent are administrated as separate formulations.

4. The method according to claim 1, wherein the cisplatin active agent comprises cisplatin and its derivative/analogues or other metallo-anticancer drugs.

5. The method according to claim 1, wherein the cisplatin toxicity reducing agent is administrated prior to administration of the cisplatin active agent.

6. The method according to claim 1, wherein the cisplatin toxicity reducing agent comprises a dimeric bismuth(III) compound.

7. A method of treating a host suffering from tumors or a cellular proliferative disease condition, comprising administrating to the host effective amounts of a cisplatin active 8. The method according to claim 7, wherein a dosage of cisplatin toxicity reducing agent is 4 to 6 fold of the cisplatin active agent.

9. The method according to claim 8, wherein the cisplatin active agent and the cisplatin toxicity reducing agent are administrated as separate formulations.

10. The method according to claim 7, wherein the cisplatin active agent comprises cisplatin and its derivative/analogues or other metallo-anticancer drugs.

11. The method according to claim 7, wherein the cisplatin toxicity reducing agent is administrated prior to administration of said cisplatin active agent.

12. The method according to claim 7, wherein the cisplatin toxicity reducing agent comprises a dimeric bismuth(III) compound.

* * * * *